United States Patent [19]
Evans

[11] Patent Number: 5,295,832
[45] Date of Patent: Mar. 22, 1994

[54] METHOD AND APPARATUS FOR CLEANING TEETH AND GUMS

[76] Inventor: Don A. Evans, 494 Turtlecreek Dr., Birmingham, Ala. 35226

[21] Appl. No.: 950,764

[22] Filed: Sep. 24, 1992

Related U.S. Application Data

[63] Continuation of Ser. No. 725,578, Jul. 3, 1991, abandoned, which is a continuation of Ser. No. 205,654, Jun. 13, 1988, Pat. No. 5,029,576.

[51] Int. Cl.$^5$ ............................................. A61C 15/00
[52] U.S. Cl. ................................................... 433/216
[58] Field of Search ......................... 433/80, 215, 216; 210/695; 128/66, 624

[56] References Cited

U.S. PATENT DOCUMENTS

| | | | |
|---|---|---|---|
| 2,939,830 | 6/1960 | Green et al. | 210/695 X |
| 3,228,878 | 1/1966 | Moody | 210/695 |
| 3,380,446 | 4/1968 | Martin | 128/24 |
| 3,514,328 | 9/1967 | Malin | 134/1 |
| 4,012,842 | 3/1977 | Vit | 32/58 |
| 4,265,746 | 5/1981 | Zimmerman, Sr. et al. | 210/695 |
| 4,302,186 | 11/1981 | Cammack et al. | 433/80 |
| 4,407,719 | 10/1983 | Van Gorp | 210/695 |
| 4,422,450 | 12/1983 | Rusteberg | 128/66 X |
| 4,501,661 | 2/1985 | Karasawa | 210/695 X |
| 4,502,497 | 3/1985 | Siahov | 433/216 X |
| 4,552,664 | 11/1985 | Renner | 210/695 |
| 4,564,448 | 1/1986 | O'Meara, Jr. | 210/695 X |
| 4,595,365 | 6/1986 | Edel et al. | 433/216 |
| 4,605,498 | 8/1986 | Kulish | 210/695 X |
| 4,659,479 | 4/1987 | Stickler et al. | 210/695 |
| 4,682,584 | 7/1987 | Pose | 433/215 X |
| 4,734,202 | 3/1988 | Mach | 210/695 |
| 4,857,204 | 8/1989 | Joklik | 210/695 |
| 4,888,113 | 12/1989 | Holcomb | 210/695 X |
| 4,957,626 | 9/1990 | Ashbrook et al. | 210/695 |

FOREIGN PATENT DOCUMENTS

| | | | |
|---|---|---|---|
| 3433417 | 3/1986 | Fed. Rep. of Germany | 210/695 |
| 2132588 | 6/1987 | Japan | 210/695 |
| 8705003 | 8/1987 | World Int. Prop. O. | 210/695 |

OTHER PUBLICATIONS

Hibben, Stuart G. "Magnetic Treatment of Water", 1-30-73.
API Publication 960, "Evaluation of the Principles of Magnetic Water Treatment", 9-85.
Transcript of the Deposition of Don Arthur Evans, Sr. dated Mar. 2, 1992.
Grutsch, J. F., and McClintock, W. J., "Corrosion and Deposit Control in Alkaline Cooling Water Using Magnetic Water Treatment at Amoco's Largest Refinery", Corrosion 84, Paper No. 330 (1984).

*Primary Examiner*—Gene Mancene
*Assistant Examiner*—Nicholas D. Lucchesi
*Attorney, Agent, or Firm*—W. Randall May

[57] ABSTRACT

A method and apparatus for cleaning and treating teeth and gums, for the removal of plaque and calculus buildup on teeth, and for the prevention of plaque and calculus formation on teeth thus reducing or eliminating susceptibility of dental and gum related diseases. The method comprises the passing of fluid particles through a magnetic field of a predetermined minimum strength wherein the fluid particles are caused to flow through the magnetic field in a south pole to north pole direction. The magnetically treated fluid is then applied to the teeth and gums. A preferred embodiment comprises a conventional, pulsating, high velocity fluid stream, tooth and gum cleaning machine for delivery of the magnetically treated fluid to the surface of the teeth and gums.

7 Claims, 4 Drawing Sheets 5,295,832

METHOD AND APPARATUS FOR CLEANING TEETH AND GUMS

This application is a continuation of Ser. No. 07/725,578, filed Jul. 3, 1991, now abandoned which is a continuation of Ser. No. 07/205,654, filed Jun. 13, 1988, now U.S. Pat. No. 5,029,576.

BACKGROUND OF THE INVENTION

I. Field of the Invention

The present invention relates to a new method and apparatus for cleaning and treating teeth and gums, and in particular, to a new method and apparatus of interrupting and arresting the natural formation of plaque and calculus on teeth.

II. Prior Art and Other Considerations

The use of magnetic fields to treat various properties of fluids, particularly water, is well-known within the realm of industrial and/or commercial activity. Typically, such treatment has been used in the prevention of scale build-up or to prevent the formation of encrustations on surfaces generally associated with the various aqueous environments inherent to such industrial or commercial activities. Devices for propelling pulsating jet streams of fluid against the surfaces of teeth and gums for the purpose of oral hygiene are well-known in the prior art.

Dental diseases are caused by microbial infections involving identified microbial populations. These populations utilize colonization as a pathogen modality and colonization is thought to be dependent upon plaque formation. Accordingly, by the prevention of plaque and calculus formation on teeth, dental diseases could also be prevented.

Due to the presence of electrovalent bonding, the removal of plaque and calculus, once formed, from the surfaces of teeth presents a very difficult task. At the present time, devices or methods for the "effective" removal of plaque and calculus from the surfaces of teeth are limited to either the metal tools and procedures used by dentists or dental personnel to scrape away such build-up or to the use of ultra sonic techniques. While both techniques have generally proven to be effective in removing plaque and calculus from the surfaces of teeth, neither technique is available to the general public without professional supervision and/or assistance and the associated expense.

SUMMARY OF THE INVENTION

An object of the invention is to provide a new teeth and gum cleaning method and apparatus.

An advantage of the invention is to provide a magnetic treatment method and apparatus which interrupts the natural process of plaque and calculus formation on teeth.

Another advantage of the invention is to provide a magnetic treatment method and apparatus which removes and controls plaque and calculus build-up on the surfaces of teeth above and below the gum lines.

Yet another advantage of the invention is to provide a safe, inexpensive, method and means for the effective removal of plaque and calculus from the surfaces of teeth for use by the public in general without the need for professional supervision or assistance.

An additional advantage of the present invention is to provide a teeth and gum cleaning method and apparatus which can be effective in the prevention and control of dental and gum related diseases.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

DETAILED DESCRIPTION OF THE DRAWINGS

Figure 1:
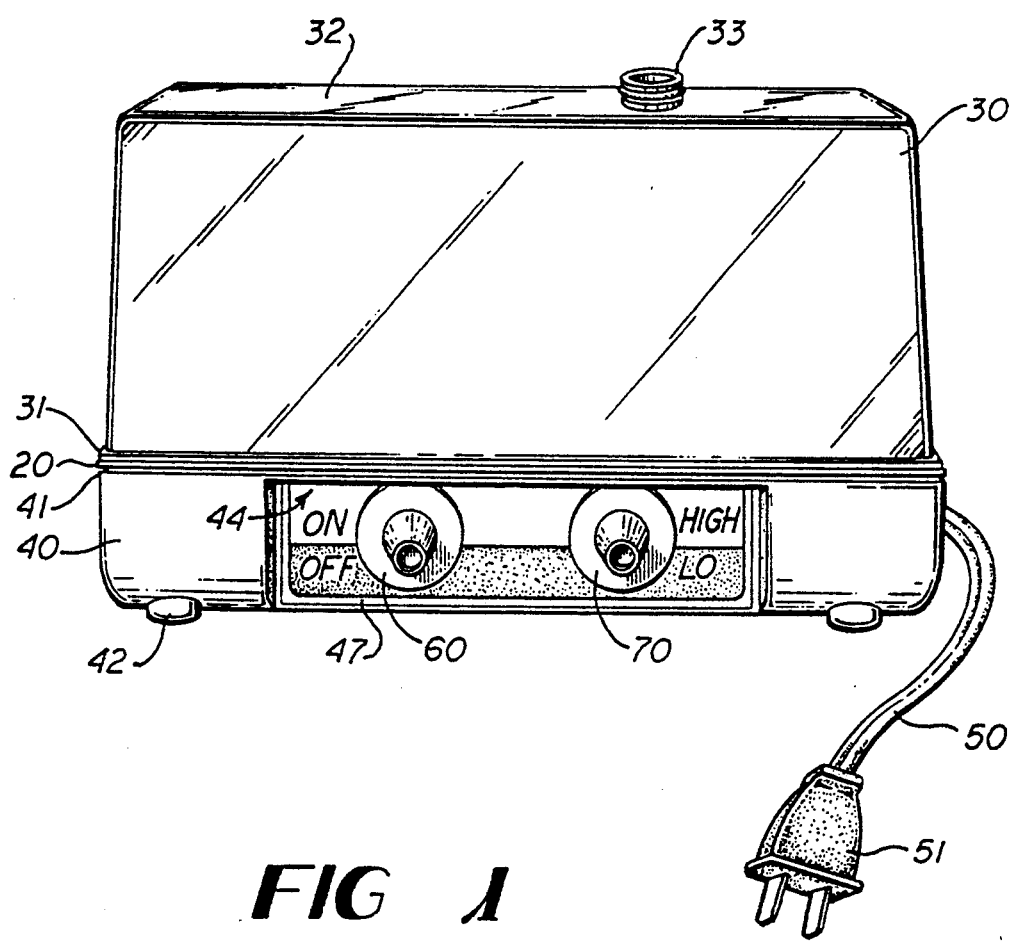
FIG. 1 is a front view of a system for cleaning and treating teeth and gums according to an embodiment of the invention with a top cover of the system in place as designed for periods of none use.
Figure 2:
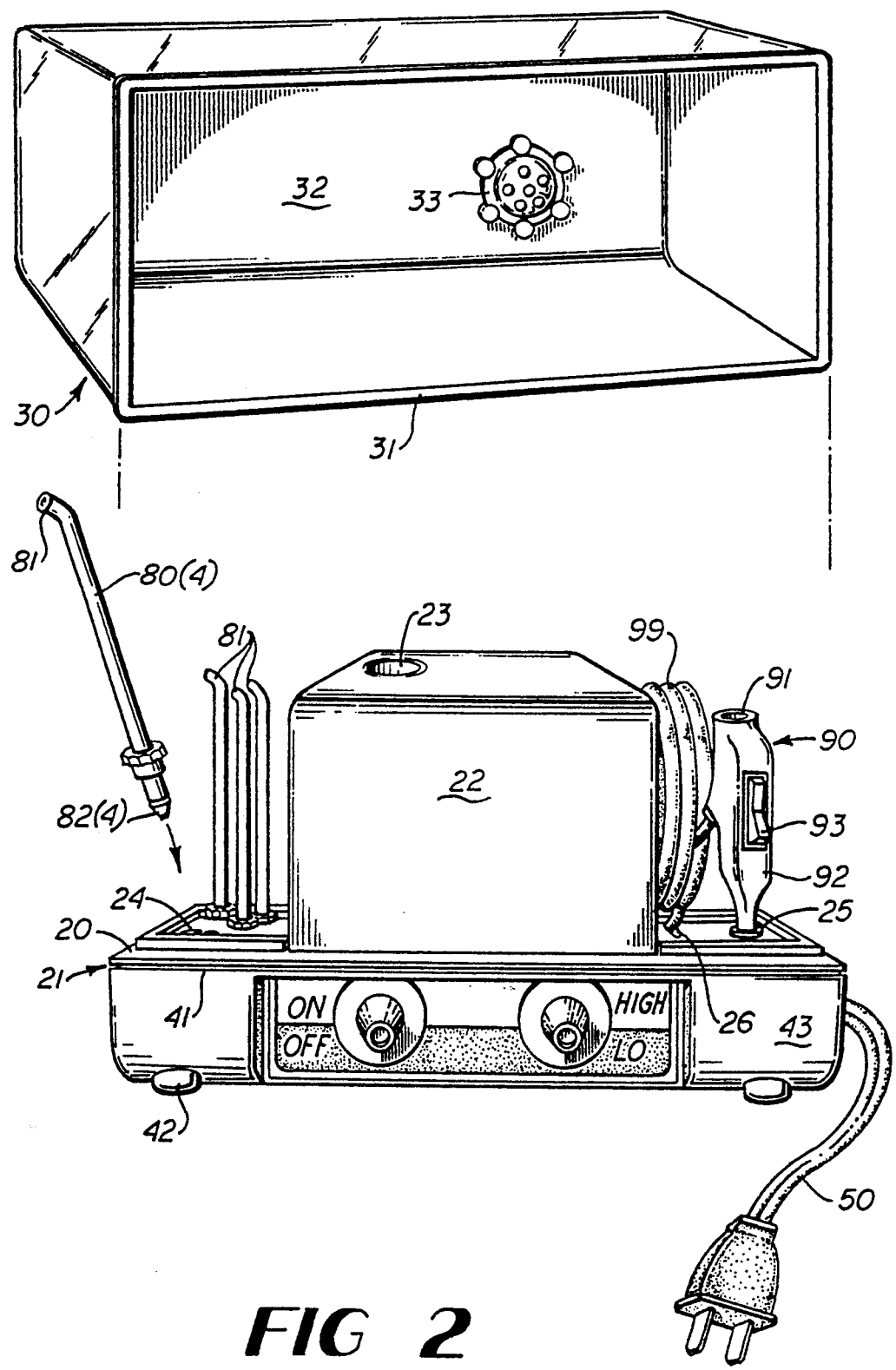
FIG. 2 is a front view of the system of FIG. 1 with the top cover removed as well as a view of the top cover lying on its side and viewed from the bottom.
Figure 3:
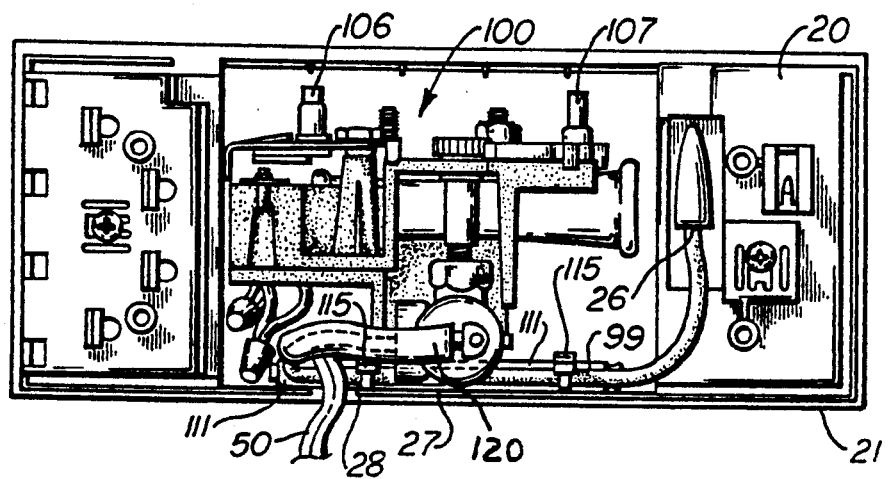
FIG. 3 is a bottom view of the system of FIG. 2 with a bottom cover removed.
Figure 5:
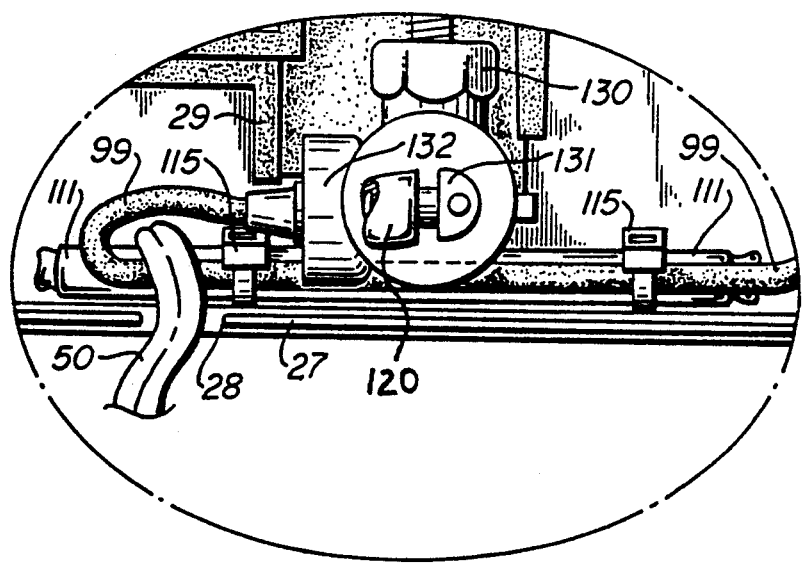
FIG. 5 is an enlarged view of the encircled apparatus of FIG. 4.
Figure 4:
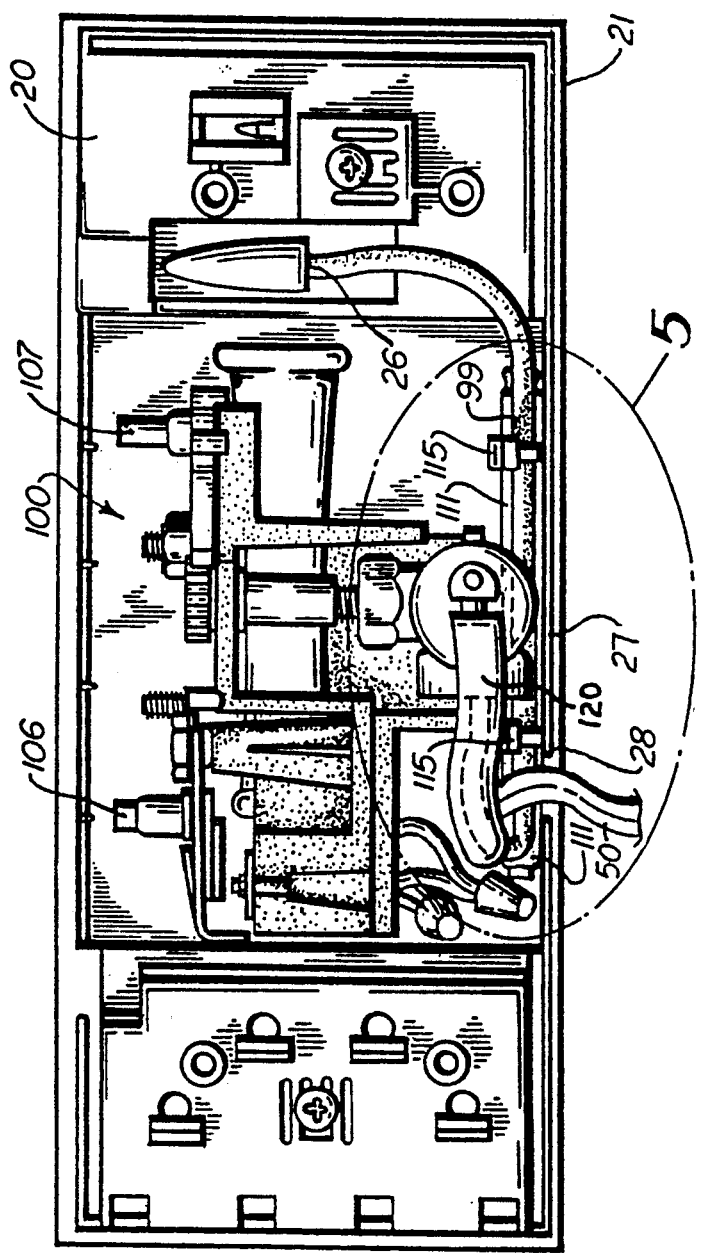
FIG. 4 is a slightly enlarged view of the system of FIG. 3 with the location of the apparatus of the embodiment of the invention encircled.

A system for cleaning and treating teeth and gums of FIG. 1, FIG. 2, FIG. 3, and FIG. 4 is typical of those employing techniques of applying to the teeth and gums, water in the form of a pulsating, high velocity stream. This system consists of a chassis 20, a top cover 30, a bottom cover 40, a power cord 50, a power switch knob 60, a pulse rate control knob 70, a set of nozzles 80, an applicator handle/controller assembly 90, and an internal mechanism 100.

The internal mechanism 100 is securely attached to the chassis 20. The bottom cover 40 is securely attached to the chassis 20. Just above a top edge 41 of the bottom cover 40, the chassis is formed into a groove 21. The chassis 20 is shaped to form a cap 22 which shrouds the internal mechanism 100. At the top of the cap 22, there is a funnel neck port 23. To the left of the cap 22, the chassis 20 is formed to have four (4) nozzle receptacles 24. To the right of the cap 22, the chassis 20 is formed to have an applicator assembly receptacle 25. Near the applicator assembly receptacle 25, there is an outlet tube port 26. Along the rear side 27 of the chassis cap 22 just below the level of the groove 21, there is a mating surface notch 28. The chassis 20, inside the cap 22, has a structural mounting protrusion 29.

The top cover 30 is generally in the shape of a rectangular box with an open bottom. In the top surface 32, there is a top cover funnel assembly 33 positioned so that when the top cover 30 is turned upside down and aligned with the cap 22 of the chassis 20, said top cover funnel assembly 31, when aligned with, fits inside the funnel neck port 23. The bottom edge 31 has a shape that is complementary to the groove 21 of the chassis 20.

The bottom cover 40 is generally in the shape of a rectangular box with an open top. On the exterior, near each corner of the bottom surface is a leg 42. The front exterior surface 43 has a recess 44. Near the center vertically, and somewhat to the left of center horizontally, of the recess 44 is a left hole 45 [not shown]. Near the center vertically, and somewhat to the right of center horizontally, of the recess 44 is a right hole 46 [not shown]. Applied to the exterior surface of the recess 44 is a label 47. Along the top edge 41 of the rear face of the bottom cover 40 is a notch 48 [not shown] at a point in alignment with the mating surface notch 28.

The power cord 50 has a standard plug 51 and passes through the bottom cover notch 48. It is connected, as required, to the internal mechanism 100.

The power switch knob 60 securely slides onto a power switch shaft 106.

The pulse rate control knob 70 securely slides onto a pulse rate control shaft 107.

It is noted that the preferred embodiment described herein has been depicted with the magnetic field created by a bar magnet. However, the magnetic field may equally as well be created by other means, such as an electromagnet or the flow of a current.

Each nozzle 80 has an input end 81 and an exit end 82. The output end 82 of each nozzle 80 is curved to facilitate the application of the cleaning fluid.

The applicator handle/controller assembly 90 consists of a handle/controller 92 and an outlet tube 99. The handle/controller 92 has a fluid flow cut-off switch 93 near the middle of the handle/controller 92. At the end of the handle/controller 92 opposite the end connecting to the outlet tube 99 is a nozzle retainer 91.

The internal mechanism 100 consists of a path for the flow, treatment and processing of water, as well as various devices providing for said processing and the control of said processing; an additional part of the internal mechanism 100 is a Alnico-V type bar magnet 111. This path includes a pump inlet tube 120 and a pump 130. The pump 130 has an inlet port 131 and an outlet port 132. The exit of the inlet tube 120 is attached to the inlet port 131 of the pump 130; this connection is leakproof. The outlet port 132 of the pump 130 is attached to the inlet end of the outlet tube 99; this connection is leakproof. The bar magnet 111 is mounted immediately adjacent to and parallel with the outlet tube 99 in the vicinity of the pump 130 inside the cap 22 using mounting bands 115. It is mounted so that a path along the outlet tube 99 from the end of the bar magnet 111 designated as the south pole to the outlet port 132 is shorter than a path along the outlet tube 99 from the end of the bar magnet 111 designated as the north pole to the outlet port 132.

The outlet tube 99 is connected from the exit port 132 of the pump 130 to the handle/controller 92.

In preparation for operation, after plug 51 is inserted into a convenient electrical outlet, the top cover 30 is removed. The applicator handle/controller assembly 90 is removed from the applicator assembly receptacle 25 in the chassis 20; one of the nozzles 80 is removed from the nozzle receptacle 24. The input end 81 of the nozzle 80 is inserted into the nozzle retainer 91 of the applicator handle/controller assembly 90. The top cover 30 is inverted and placed on top of the chassis cap 22 so that the top cover funnel assembly 33 is aligned with, and fits inside, the funnel neck port 23.

The top cover is filled with tap water, the power is turned on using the power switch knob 60. The pulse rate is set to a desirable level using the pulse rate control knob 70.

The output end 82 of nozzle 80 is aimed at the desired area of the teeth and/or gums and the fluid flow cut-off switch 93 is slid in the direction of the nozzle allowing the water flow to begin.

In operation, the water flows form the inverted top cover 30 through the top cover funnel assembly 33 and the funnel neck port 23 into the internal mechanism 100.

The internal mechanism 100 is a unit which receives water from the inverted top cover 30 and power from the power cord 50 and delivers magnetically treated water in a pulsating, high velocity stream through the outlet tube 99.

The path of the water through the internal mechanism 100 begins at the funnel neck port 23 and continues through the inlet tube 120 to the inlet port 131 of the pump 130. The water exits the pump 130 through the outlet port 132 and exits the internal mechanism 100 through the outlet tube 99.

Advantageously, water passing through the outlet tube passes through the magnetic field emanating from bar magnet 111.

The magnetically treated water continues its journey through the outlet tube 99 through the applicator handle/controller assembly 90 and through the nozzle 80 whereupon it is delivered to the surfaces of the teeth and/or gums.

Water so magnetically treated and applied to the teeth and gums not only removes plaque and calculus build-up but also prevents such formation thereby reducing or eliminating susceptibility to dental and gum related diseases.

While the invention has been particularly shown and described with reference to the preferred embodiments thereof, it will be understood by those skilled in the art that various alterations in form and detail may be made therein without departing from the spirit and scope of the invention.

What is claimed is:

1. A method for the treatment of deposits, including plaque, calculus, or the like, on the teeth in the oral cavity of an individual, comprising the steps of:
    a) providing means for delivering fluid from a location that is accessible to, and controllable by, the individual along a flow path eventually arriving at the oral cavity of the individual;
    b) creating a magnetic field along the flow path, the magnetic field terminating prior to the point that the flow path enters the oral cavity;
    c) passing the fluid through the magnetic field prior to the arrival of the fluid in the oral cavity; and thereafter,
    d) applying the fluid to the teeth in the oral cavity of the individual, whereby the harmful effects of the deposits on the teeth are reduced.

2. The method of claim 1, wherein the delivery of the magnetically treated fluid is accomplished by propelling said fluid against the surfaces of the teeth and gums by using a fluid pump capable of producing pulsating, high velocity jet streams.

3. The method of claim 1, wherein said magnetic field is produced by a permanent magnet.

4. The method of claim 3, wherein said permanent magnet is a bar magnet.

5. The method of claim 3, wherein said permanent magnet is an Alnico-V type bar magnet.

6. The method of claim 1, wherein said magnetic field is produced by electric current.

7. The method of claim 1, wherein said fluid is water.

* * * * *